United States Patent [19]

Besendorfer et al.

[11] Patent Number: 5,184,070
[45] Date of Patent: Feb. 2, 1993

[54] EDDY-CURRENT DEFECT TEST INSTRUMENT WITH MULTIPLE TEST PROBES AND ONE DISTANCE PROBE

[75] Inventors: Herman Besendorfer, Altenriet; Gunter Stritzke, Gomaringen; Franz Haditsch, Reutlingen, all of Fed. Rep. of Germany

[73] Assignee: Institut Dr. Friedrich Forster Pruferatebau, Reutlingen, Fed. Rep. of Germany

[21] Appl. No.: 647,752

[22] Filed: Jan. 29, 1991

[51] Int. Cl.[5] .................... G01R 33/12; G01N 27/72; G01N 27/82
[52] U.S. Cl. .................... 324/225; 324/238; 324/262
[58] Field of Search ............... 324/225, 226, 236–243, 324/262

[56] References Cited
U.S. PATENT DOCUMENTS
4,792,755 12/1988 Huschelrath et al. ........... 324/242

Primary Examiner—Walter E. Snow
Attorney, Agent, or Firm—George J. Netter

[57] ABSTRACT

An eddy-current defect test instrument with a rotary head (30) and test probes (32, 34, 36, 38) offset-mounted along a circular track (66) with only one distance probe (40) to achieve compensation for variations in spacing between the probes and the workpiece which only requires one distance signal processing device (60) and only one rotary transmitter (100). This is accomplished by storing the control signals obtained from the distance probe during one revolution of the rotary head (30) and retrieving those control signals associated with the probe position and appropriately modifying a defect signal.

16 Claims, 2 Drawing Sheets

EDDY-CURRENT DEFECT TEST INSTRUMENT WITH MULTIPLE TEST PROBES AND ONE DISTANCE PROBE

BACKGROUND OF THE INVENTION

1. Field of the Invention

The present invention relates generally to non-destructive testing of objects for defects, and, more particularly, to an eddy-current test instrument providing compensation for variations in spacing from a workpiece surface.

2. Related Art

Eddy-current test instruments having a rotary head have been used for some time in the non-destructive testing for defects of materials. Nearly equally long, at least since the introduction of non-sliding test probes, has been the application of spacing compensation means for such devices (U.S. Pat. No. 3,281,667; German patent application 1,773,501). Such distance compensation has been found necessary, as otherwise a reasonable evaluation of the defect signals conforming to the depth of the defect would not have been possible, since defect signals are subject to substantial variations in sensitivity because of the unavoidable distance variations.

Early spacing compensation means employed controllable amplifiers having a non-linear control characteristic as the primary control elements. It was necessary, however, that the characteristic curve have a specific shape, in order to accommodate the fact that the distance signal and the sensitivity variation of the defect signals relates differently to the probe distance from the workpiece. Compromises, therefore, had to be accepted with respect to obtainable control accuracy. Also, replacing probes having different characteristics was problematic, if not impossible.

These problems have been partially overcome by distance compensation relying on a digital control system having a linearly controllable signal amplifier and the combination of the distance functions was achieved by adequately dimensioned resistance chains (German patent publication 2,530,816).

An important disadvantage, however, of the techniques used up to now is that for each test head offset mounted on a circular track, a complete distance compensation with distance probe, distance signal processing and network is required for the combination of the distance functions. This is based on the fact that the sources for distance variations (e.g., eccentricity and out of roundness of the part to be tested) have different effects at any given time for each point of the circular track, and, therefore, for each of the offset mounted test heads. As with rotary heads, there is always required a signal transmission from rotating to stationary parts, and there is also required for the distance signals of each test head its own transmission channel (e.g., in the form of a rotary transmitter). Because of the large number of transmission channels required anyway, this latter requirement is very often hard to achieve.

SUMMARY OF THE DISCLOSURE

It is a primary aim and object of the present invention to provide an eddy-current test instrument wherein distance compensation for a plurality of offset mounted test heads along a circular track is provided by only one distance probe.

It is assumed initially that the shape and location of the test instrument circular track can be regarded as constant, and that, with the high rotary speeds of common rotary heads, the position of the part to be tested will only be slightly modified within one head revolution. This makes it possible and reasonable to monitor and store the geometry of the part to be tested within one revolution, to be able to use one distance probe only, and to access adequate information for each of the existing test heads to perform the distance compensation correctly with respect to position. The greater the number of test heads used in the described instrument, the greater the advantages obtained. But even with only two test heads, there are considerable savings because of the omission of a second distance probe with associated signal processing stage and transmission channel. When the number of transmission channels is given (e.g. by using a given rotary transmitter arrangement), for each test head exceeding one, one transmission channel will be made free and can be utilized by another test channel.

According to a first embodiment of the invention, test instrument positions along the circular path are provided by control signals obtained during one revolution and stored in a first table, all of which is made possible in a simple way by generating clock pulses and have these pulses synchronized by a pulse transducer mounted along the circular track. Furthermore, several successive circumference clock pulses are combined with a scanning clock pulse, and with storing and retrieving of the control signals performed during the clock pulse period of the scanning clock pulse.

According to another embodiment of the invention, an analogous distance signal is digitized by means of an a-d converter. With a digital distance signal obtained therefrom, an auxiliary signal corresponding to the height or distance of the probe is obtained from a second. With such auxiliary signal, a digital control signal is taken from a third table, this digital control signal being, then, stored, in the above-mentioned first table for later retrieval.

According to another embodiment of the invention, the procedure of distance compensation is controlled by a micro-computer. Further, according to still another embodiment of the invention, the distance signal from a distance probe is first rectified in a controlled rectifying stage to provide a vector signal having two components, from which is then formed an amount signal in a vector amount generating stage.

DESCRIPTION OF THE DRAWING

In the accompanying drawing:

FIG. 4 is a function block diagram of an eddy-current test instrument of this invention.

DESCRIPTION OF PREFERRED EMBODIMENTS

Figure 1:
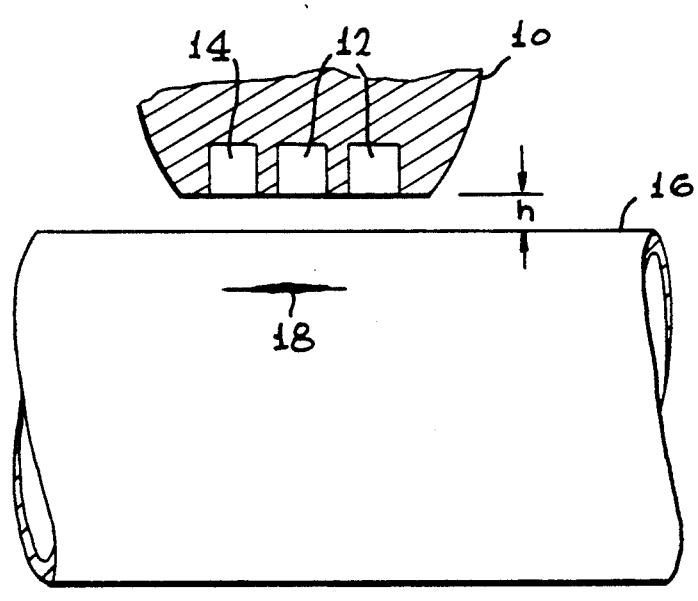
FIG. 1 is an elevational view of a test head shown in operative relation to a workpiece.

In FIG. 1, there is shown in simplified manner a section through part of a test head 10 belonging to a rotary head of an eddy-current test instrument. The test head 10 includes two defect probes 12 and one distance probe 14 scanning the surface of a tubular part 16 to be tested which is moving in the direction of the arrow as well as being provided with a relative rotation motion with respect to each other. The spacing between the probes 12, 14 and the part outer surface distance h, is constant only so long as the test instrument rotation is carefully controlled and an accurately circular cross section of the part 16 to be tested can be assumed. In practical procedures, movement or guidance errors and shape errors occur and must be taken into account. When, for example, an eccentricity with the value a is present, the distance h will vary following a sine function with the amount a. Defect signals derived in the probes 12 from a defect 18 are subject to corresponding spacing variations depending upon where the defect is located.

Figure 2:
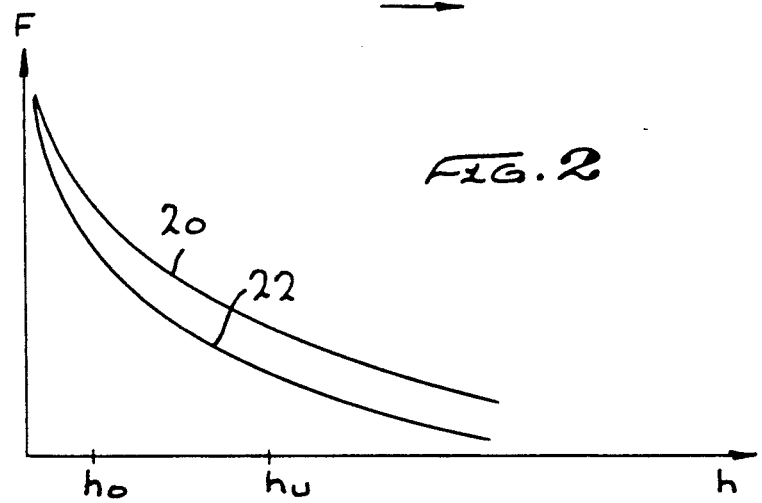
FIG. 2 is graph of defect signal characteristics.

In FIG. 2, there are shown two curves 20, 22 representing two different probe types, and from which it is seen how the amplitude F of a defect signal varies as a function of the distance h. Besides the probe type, there are other factors determining the shape of curves 20, 22 (e.g., the test frequency, test material and geometry of the part to be tested).

Figure 3:
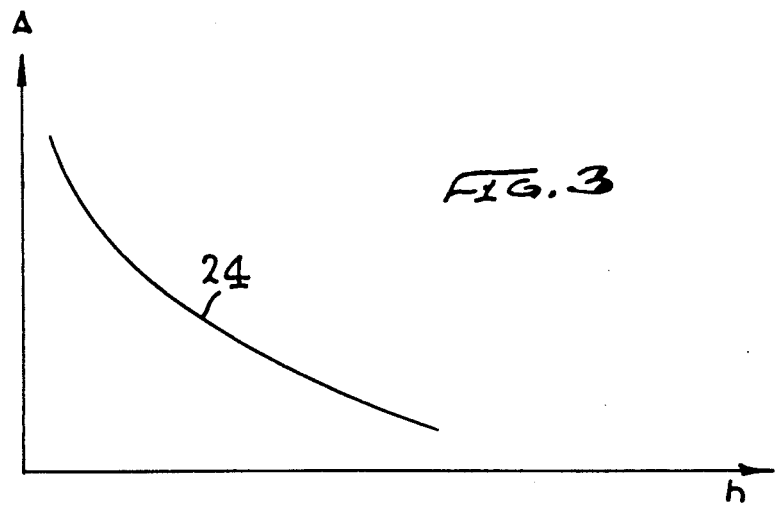
FIG. 3 is a graphical representation of distance signal characteristics.
Figure 2:
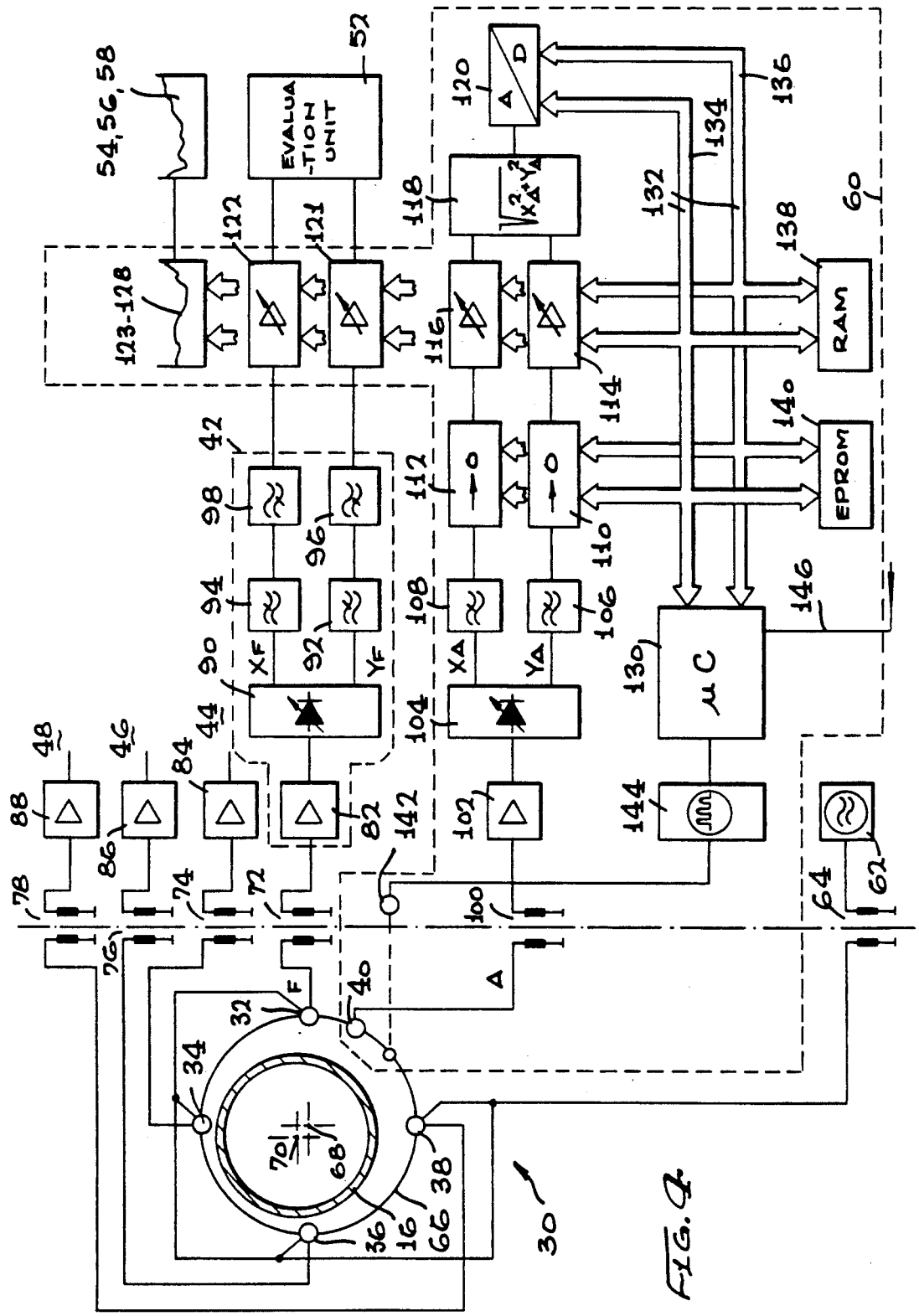

It is an object of every distance compensation technique to eliminate the dependence of the defect signal F on the distance h over a sufficiently large operating range, e.g., from ho to hu. The distance probe 14 accordingly delivers a distance signal A, the dependence of which on the distance h may correspond to a curve 24 as in FIG. 3, if an eddy-current probe is used as the distance probe. Also in this case, the shape of curve 24 will be determined by the factors named above. When combining the signals $A = f(h)$ and $F = f(h)$ for the purpose of distance compensation, it must be assumed that each relevant variation of one of the factors will also have a consequence, a variation of the shape of the respective curve to be taken into account, when the distance compensation is expected to be effective. This is, as will be more particularly described, easily accomplished within the framework of this invention.

The block diagram of FIG. 4 depicts in simplified representation the overall configuration of an eddy-current test instrument according to the invention, which can be split generally into a rotary head 30 with test probes 32, 34, 36 and 38 and a distance probe 40; a series of signal processing devices 42, 44, 46 and 48, of which only one (42) is completely shown and wherein the defect signals from the test probes 32-38 are processed; a corresponding series of evaluation units 52, 54, 56 and 58, only one of which is represented; and a distance compensation device 60, wherein distance signals are derived, processed and used for distance compensation.

The test probes 32-38 of rotary head 30 are mounted into four test heads offset by 90° relative to each other. They are supplied with a.c. voltage by a generator 62 via a rotary transmitter 64. As indicated in FIG. 1, instead of the one test probe used here, several test probes can be present side by side in the test head, so as to achieve a larger scanning width. In operation, the test probes 32-38 follow a circular track 66 about a center 68. Relative to the latter, the axis 70 of the part 16 to be tested is shown displaced, so that the distance h between the surface of the part to be tested and the test probes 32-38 varies periodically following a sine function.

The defect signals from the test probes 32-38 are fed over rotary transmitters 72, 74, 76 and 78 to the respective inputs of amplifiers 82-88 belonging to signal processing devices 42-48. For space reasons, the signal processing devices 44-48 are not completely represented here although it is to be understood that they can be identically constructed to signal processing 42. With respect to signal processing device 42, the defect signal F from amplifier 82 is led to the input of a controlled rectifier 90, wherein it is split into two defect signal components $X_F$ and $Y_F$. They are freed in low-pass filters 92, 94 from interference signals of higher frequency, e.g., the carrier frequency, and in high pass filters 96, 98 from interference signals of lower frequency, e.g., the rotational frequency of the rotary head 30.

An evaluation unit 52-58 has connection to each of the signal processing devices 42-48 which may include usual evaluation means, e.g., display on a screen and recording, and, in particular, a computer aided defect signal analyzer.

The condition for a fair evaluation is, as already mentioned, a sufficient distance compensation in a compensation device 60. The latter is based substantially on the distance probe 40 and supported together with the test probe 32 by a common test head. The distance signal produced therein passes over a rotary transmitter 100 and an amplifier 102 to the input of a controlled rectifier 104, where it is decomposed into two distance signal components $X_A$ and $Y_A$ being arranged vertically to one another. Controlled rectification has proven reasonable and useful, in contrast to former experience for preventing possible falsification of the distance signal. Over low-pass filters 106, 108, the signal components $X_A$, $Y_A$ are conducted to the input of zero adjusting stages 110, 112. The latter serve to free the signal components $X_A$, $Y_A$ from offset voltages resulting from adjustment errors of the distance probe 40 and on stray effects, in particular in the rotary transmitter 100. For this purpose, the offset voltage at the inputs of the zero adjusting stages 110, 112 is determined with no part being tested by the rotary head, and a compensation voltage of equal amplitude, but opposite polarity, is superimposed. Furthermore, the signal components $X_A$, $Y_A$ pass over adaptation amplifiers 114, 116 and an amount generating unit 118 to the input of an analog/digital converter 120. The two adaptation amplifiers only serve the purpose of adapting the distance signal to the operating range of the distance compensation. This adaptation is preferably done with the maximum possible distance signal voltage, that is, with minimum possible distance $h=0$ between surface of the part to be tested and the distance probe 40. In the amount generating stage 118, analogous computation means performing the calculation $(A) = \sqrt{(X^2_A + Y^2_A)}$. The analogous value A is then converted into a digital distance signal required for the distance compensation, i.e. for controlling a series of digital control elements 121-128 connected between the signal processing devices 42-48 and the evaluation units 52-58. Each of the signal components $X_F$, $Y_F$ of the four signal processing devices 42-48 requires its own control element, i.e., in total eight.

The output of the distance compensation, the zero adjustment and the amplification adaptation are fed to a micro-computer 130. In particular, the computer is connected for this purpose over a bus 132 with the a-d converter 120, the control elements 121-128, the zero adjusting stages 110, 112 and the adaptation amplifiers 114, 116. To the bus 132 transmitting addresses and data over channels 134 and 136 there are further connected a first (138) and a second (140) digital storage element. The first digital storage element 138 which is a RAM serves for storing three tables I, II and III, the tasks of which will be explained later. The second storage element 140 which is an EPROM contains the program for the procedure named above.

Table II is derived from the function $(A)=f(h)$ and relates an address corresponding to the value h. Table III is derived from the function $F=f(h)$ and provides auxiliary digital signals used as a factor in the digital multiplier, by which the defect signal components $X_F$ and $Y_F$ have to be multiplied in order to be independent of the distance h effect, i.e. from the required control signal.

The control elements 123-128 belonging to the test probes 34, 36, 38 are needed for determining the required control signal from Table I in which control signals as a function of peripheral position are stored. For this purpose, a pulse transducer 144 controlled by the micro-computer 130 delivers information to the computer. The pulse transducer 142 operates with a light barrier, the light beam of which is interrupted once per revolution of the rotary head 30 and delivers a pulse to synchronize a series of clock pulses (e.g. 360 per circumference) generated in the pulse circuit 144. If, for example, three or six successive circumference clock pulses are combined in a scanning clock pulse, there will result per revolution 120 or 60 scanning clock pulses, respectively. In order that an integer number of scanning clock pulses is obtained on the path from test head to test head, the number of scanning clock pulses per revolution must be a multiple of the number of test heads, which is the case here in either assumption. For smaller diameters of the part to be tested or with minor requirements, 60 scanning clock pulses may be sufficient. Loading and retrieving Table I takes place within the clock pulse period of a scanning clock pulse. During each clock pulse period, Table I is updated by storing the actual information of Table III at the correct position in Table I, i.e. at the address conforming to the peripheral position of the distance probe 40. Then, Table I is accessed with the address conforming to the peripheral position of a test head, and the respective information stored during the previous revolution is delivered to the control element corresponding to the test head. In this way, all control elements 123-128 are supplied with adequate control signals.

The digital control elements 121-128 are essentially devices the amplifying gain of which is controlled by a digital signal. An excellent device for use in this connection is a quad 8-bit multiplying CMOS digital-to-analog converter with memory which is sold by Precision Monolithics, Inc. under the trade designation DAC-8408. The digital control elements 121 and 122 obtain distance control information directly since the distance measuring element is typically at the same position as probe 72 while elements 123-128 receive their distance according to the angular relations of the probes 74-78.

The described mode of operation with Tables II and III is very advantageous when the distance probe is to be replaced by another one having a different characteristic, or when test probes are to be replaced by a different type, or when the characteristics of the probes may vary due to changing parameters. In this latter case, Table II and/or III can be reloaded temporarily and without having to spend larger efforts from outside by corresponding auxiliary memories. For this purpose, as well as for the first time loading of the tables, the microcomputer 130 is provided with an input 146 for a host computer. Working with two separate tables II and III has still another advantage. The digital auxiliary signal from table II corresponding directly to the distance h can be lead towards the outside and can be used for additional monitoring tasks.

What is claimed is:

1. An eddy-current test instrument having a rotary head provided with at least two test heads including eddy-current test probes offset mounted along a circular track for scanning a part to be tested; signal processing devices by means of which defect signals in the test probes are derived from defects in the part to be tested and wherein such defect signals are further processed; evaluation units wherein defect signals are evaluated; distance compensation devices wherein defect signals are compensated with respect to the distance h between the test probes and the part to be tested, including a distance probe wherein a distance signal is derived from the distance h, a signal processing device wherein the distance signal is processed to a control signal, and control elements connected between the signal processing devices and the evaluation units, said control elements modifying the defect signals as a function of control signals, comprising:

a single distance probe and one signal processing device;

means for providing control signals derived during one revolution of the distance probe identifying the peripheral position of said distance probe and storing the control signals in a first table (I); and means responsive to a test probe passing a peripheral position for retrieving the control signal for this peripheral position and for controlling the control element(s) belonging to the respective test probes of said test head by the retrieved control signals.

2. An eddy-current test instrument according to claim 1, in which the means for detecting the peripheral position as a function of the rotational frequency of the rotary head includes circumference clock pulses generated in pulse circuitry which circumference clock pulses are synchronized by at least one pulse transducer mounted on the circular track.

3. An eddy-current test instrument according to claim 2, in which there is further provided means for providing a scanning clock pulse including a series of successive circumference clock pulses, each said scanning clock pulse corresponding to a particular peripheral position, retrieving of control signals being within the scanning clock pulse period.

4. An eddy current test instrument according to claim 3, in which the number of scanning clock pulses is a multiple of the number of test heads.

5. An eddy-current test instrument according to claim 1, in which the distance signal is digitized in an A/D converter and the digitized distance signal actuates means for retrieving a digital auxiliary signal directly corresponding to the distance H from a second table (II); means responsive to the digital auxiliary signal for retrieving a digital control signal from a third table (III); and means for storing the digital auxiliary signal in the said first table (I).

6. An eddy-current test instrument according to claim 5, in that the digital control signal is applied directly to the control inputs of the control elements wherein the position of the distance probe coincides with the position of the test probes belonging to said control elements.

7. An eddy-current test instrument according to claim 5, in which said tables I, II and III are stored in a first digital memory element.

8. An eddy-current test instrument according to claim 7, in which an A/D converter, the control elements, and first digital memory element are connected through a bus with a micro-computer controlling the procedure of distance compensation.

9. An eddy-current test instrument according to claim 8, in which the operating program for the control of the procedure of distance compensation is stored in a second digital memory element also connected to the bus.

10. An eddy-current test instrument according to claim 4, in which the means for providing a scanning clock pulse is controlled by the micro-computer.

11. An eddy-current test instrument according to claim 1, in which the distance signal of the distance probe is rectified in a controlled rectifier circuitry to form a vector signal having two components ($X_A$, $Y_A$), from which is then formed in a vector amount generating device an amount signal.

12. An eddy-current test instrument according to claim 11, in which adaptation amplifiers are controlled by the micro-computer and the amount signal is determined for a given distance from the corresponding value in table (II) for the given distance.

13. An eddy-current test instrument according to claim 1, in which elimination of a residual voltage superimposed on the distance signal is controlled by the micro-computer by adding to the input voltage of the residual voltage compensation an auxiliary voltage corresponding in its amount to the residual voltage and having the opposite sign.

14. An eddy-current test instrument according to claim 1, in which the micro-computer is connected with a host computer over a communication link.

15. An eddy-current test instrument according to claim 14, in which the tables II and III are loaded from the second digital memory element.

16. An eddy-current test instrument according to claim 14, in which the tables II and III are stored in the host computer.

* * * * *